United States Patent
Gordon et al.

[19]

[11] Patent Number: 5,947,987
[45] Date of Patent: Sep. 7, 1999

[54] TISSUE REMOVAL

[75] Inventors: Eugene Irving Gordon, Mountainside; Parid Turdiu, West New York, both of N.J.

[73] Assignee: Medjet, Inc., N.J.

[21] Appl. No.: 08/955,539

[22] Filed: Oct. 22, 1997

[51] Int. Cl.⁶ ..................................................... A61F 9/00
[52] U.S. Cl. ......................................... 606/166; 606/167
[58] Field of Search ............................... 606/1, 166, 167, 606/159; 128/898; 600/401

[56] References Cited

U.S. PATENT DOCUMENTS 5,139,518  8/1992  White ....................................... 606/166

FOREIGN PATENT DOCUMENTS

| 0238196 | 8/1986 | German Dem. Rep. .............. | 606/166 |
| 3433581 | 3/1986 | Germany ................. | 606/166 |
| 1337068 | 9/1987 | U.S.S.R. ................. | 606/166 |

*Primary Examiner*—Glenn K. Dawson
*Attorney, Agent, or Firm*—Graham & James LLP

[57] ABSTRACT

A method for improving integrity and accuracy of removal or hinged removal of elevated tissue layers particularly of a cornea. The area of tissue removal is isolated from remaining tissue by a shallow complete perimeter cut, substantially normal to the tissue surface. With a cornea, a perimeter in the form of a circumference is shallowly scored into the cornea tissue for a depth somewhat greater than that of the tissue to be removed (and of an appropriate diameter) by means of a surgical trephine. Corneal tissue, normally under tension tends to separate at the score site to form a groove with the circumscribed area becoming additionally slightly elevated from the adjacent corneal tissue because of release of tension across the groove site. Lateral edges of the circumscribed area are free of surface layer tissue which is harder to cut at an angle to the layer. Lateral cutting of the corneal tissue which extends above the groove is a perfect cut of a cylindrical slice with use of a cylindrical trephine. To form a hinged layer the lateral cutting is terminated before completion with the remaining tissue functioning as the hinge. Epithelium tissue is not carried into the slice or interface of the cut tissue and stroma.

7 Claims, 1 Drawing Sheet

TISSUE REMOVAL

FIELD OF THE INVENTION

This invention relates to procedures for effecting lateral tissue slicing or excision and particularly to corneal tissue which is removed in layers for refractive correction or for other medically required reasons.

BACKGROUND OF THE INVENTION

Because of the nature of the human eye and its characteristics of free movement in an eye socket, it is imperative that the eye be restrained during the cutting or shaping of the cornea thereof. In U.S. Pat. No. 5,556,406, issued Sep. 17, 1996, and owned by the assignee of the present application, there is described a technique for holding the anterior cornea surface with a template during the cutting thereof with a waterjet surgical cutting device, in a refractive vision correction procedure. This helps to stabilize the cornea during the cut and, in fact, it seems to be essential to get a smooth cut. The template works particularly well when it is provided with a layer of sharp microscopic size particles or other similar structural elements on the surface of the template which bite into the cornea surface as the cornea is pressed against the template. This further helps in preventing lateral motion of the cornea surface during the cutting. Movement stability during cutting, even with a waterjet, is essential since dimensional tolerances of microns are required in order to achieve accurate corneal refraction correction.

Surgical knife blade-based (microkeratomes) are unable to achieve such accuracies even with effective corneal restraint. With use of a surgical knife blade to cut through the cornea, corneal tissue slips and slides past the blade, the tissue is compressed and distorted, and the cut layers are wedged, rippled, striated, etc. A good analogy to the action of this blade based microkeratome is the operation and inadequacies of a carpenter's plane. In addition, epithelial material, dragged in by the blade, may be left on the interface between the cut layers, which, after the layer is replaced, may grow later within the stroma and cause significant difficulties. Tiny chips of the blade edge may also be left imbedded in the stroma. None of this occurs with a waterjet cut. It should also be noted that a surgical blade has a wide portion of at least 150 microns of the blade part, as distinct from the edge, and this must displace tissue as it cuts. Thus, the forces on the tissue are larger.

A waterjet of a waterjet tissue cutting system may be made to operate readily at pressures as high as 20,000 psi, with a scan of the waterjet beam across the cornea at speeds well above 10 mm per second. At such speeds the waterjet moves a distance equal to its own diameter in a few milliseconds, faster than the cornea can respond mechanically to the forces exerted by the waterjet. Thus, under such conditions the cornea behaves almost like a rigid body, but without the drawbacks of an actual rigid body, an ideal situation for precise cutting. However, with normal lateral cuts effected through the cornea, a waterjet still encounters layers (epithelium, Bowman's layer, stroma) of varying density and toughness which may detrimentally affect cutting control, accuracy and integrity of cuts. In addition, the lateral action of the waterjet is similar to a cut with a drawn blade. The waterjet laterally "cuts" from its leading edge by effecting a separation between lamellae of corneal tissue during scanning rather than by actually cutting through the lamellae which is a lower energy procedure. If the waterjet is also required to effect the initial cross lamellae cut excessive energy is required for the waterjet during the cutting procedure.

With a prior art lateral waterjet cut through the corneal tissue there is an initial incision through the curved outer surface of the cornea. Thus, the beginning and end of the cut are oblique cuts through the tough outer layer surface of the cornea (epithelium and Bowman's layer) before a cut is effected in the stroma tissue as desired. A gutter formed with the lateral cut is not perfectly defined and there is some residual structure at the boundary transition.

The keratomileusis (lamellar keratoplasty) procedure is one involving lateral cuts of corneal tissue which initially involves surgical removal, with a microkeratome, of a uniform thickness button or lenticule of corneal tissue of a thickness containing the epithelium layer, Bowman's membrane (intact) and a portion of the stroma. The button or lenticule preferably remains hingedly attached at one point to the cornea as a replaceable flap. The lenticule is moved out of the way, the stroma bed is then surgically reshaped, with a knife blade or laser, as required, and the lenticule is replaced. However, the lack of a perfect fit of the flap on the stromal bed, when the scalpel type of microkeratome is used, is a source of irregular astigmatism.

SUMMARY OF THE INVENTION

It is an object of the present invention to provide a method and device for improving accuracy and integrity of removal of sub-surface tissue, and particularly corneal stromal issue without damage to cut lamellae or introduction of foreign material into contact therewith.

It is a further object of the present invention to provide such method and device wherein only the lamellae of the stroma are cut or separated with lateral cuts.

Generally the present invention comprises a method of effecting facilitated lateral cuts of normally stressed sub-surface tissue such as corneal stroma tissue, by means of moving, though not removing, other layers out of the path of direct lateral cuts. The method comprises the steps of:

a) peripherally shallowly scoring an area of the sub-surface normally stressed tissue, which is to be laterally cut, to a depth whereby the sub-surface tissue, is released from lateral stress and becomes exposed for lateral cutting access at the score site; and b) effecting at least one lateral cut into the exposed sub-surface tissue.

The scoring may be adapted for complete removal of tissue with a totally peripherally enclosing score and a complete lateral cut from score wall to score wall, or the initial score may be incomplete in a peripheral enclosure to allow a small, non-scored surface tissue area to function as a hinged area of the surface tissue for direct replacement on the cut sub-surface tissue surface. Alternatively, and most preferably, the scoring is totally peripherally enclosing and the lateral cut is stopped prior to completion whereby a portion of the sub-surface tissue, e.g., stromal tissue, forms a hinge for the flap, as used in ALK procedures.

The depth of the shallow score is such that stress relief causes a sufficient amount of the circumscribed sub-surface tissue area to become elevated for direct access of lateral cutting for the desired amount of sub-surface tissue removal. As a result, a waterjet beam of lesser energy can be utilized with the procedure of the present invention (wherein the waterjet does not need to effect an initial cut through the lamellae) and the waterjet can be made to operate faster, with a smaller diameter beam and at a lower operating pressure, all with reduced tissue trauma.

The score is preferably normal to the plane of the tissue (e.g. cornea) whereby the circumscribed sub-surface tissue is cut and removed by the lateral cuts in layers corresponding to circular lateral cuts of a cylinder. Other scoring cuts, which are not normal but angularly offset, which provide the stress relief are also within the purview of the present invention but are more difficult to implement.

The present invention further comprises a device which effects the peripheral scoring and preferably comprises a trephine in combination with means for holding and shaping the anterior surface of the cornea in position during the scoring and lateral cutting, such as a vacuum template.

These and other objects, features and advantages of the present invention will become more evident from the following discussion and drawings in which:

SHORT DESCRIPTION OF THE DRAWINGS

FIG. 1 schematically depicts prior art lateral cutting of corneal tissue which includes cuts through low sectility outer surface layers;

DETAILED DESCRIPTION OF THE INVENTION

Figure 1:
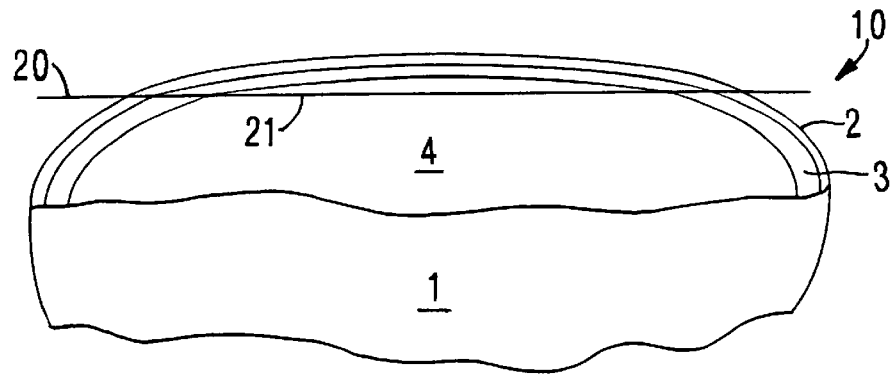

In a preferred embodiment of the present invention a sharp surgical trephine is used to cleanly effect the score. In corneal tissue the score cuts through the epithelium layer and the Bowman's layer and into the stroma. As a result of stress relief from the score cut, the peripherally enclosed tissue contracts laterally and elevates. This elevation of the tissue renders a peripheral area of the sub-surface stroma directly accessible for the lateral cutting, without necessity for cutting across epithelial, Bowman's layer tissue, or stromal tissue, thereby obviating the prior art problems encountered with lateral cutting of the epithelium and Bowman's layer.

In contrast to prior art lateral cutting of a cornea, such as in keratomileusis (lamellar keratoplasty) procedures, the resulting boundary and gutter of the trephine precut cornea are extremely cleanly defined. There is no chance of epithelial material depositing on the cut interfaces since with the trephine scoring, the waterjet beam never encounters epithelium. Additionally, with the trephine scoring, neither the flap nor the underlying stromal bed are under lateral tension during the cut so there is no relaxation of tension as the lateral cut progresses. After effecting the cut, the resulting flap is perfectly defined and fits perfectly on the bed with the cut being extremely clean.

The use of a preliminary scoring step together with a lateral waterjet cut allows production of perfectly fitting, extraordinarily clean flaps of precise uniform thickness, typically in the range of 100 to 150 microns as chosen in advance by the spacing of the waterjet from the template. The v-shaped gutter or groove, formed with the scoring, can be expected to heal quickly as epithelium first fills the space and then collagen closes the gap much as happens in the deep radial or arcuate cuts in radial or astigmatic keratotomy or the gutters of microkeratome cut corneas. The circular gutter will develop some haze as does the gutter region in keratomileusis but it is totally outside the vision zone.

In a highly preferred embodiment of the present invention the trephine is used in conjunction with a template used to immobilize the cornea during the lateral cutting. The trephine in such embodiment is a right circular cylinder made of stainless steel with one end sharpened and it is positioned to concentrically surround the circular template which has a diameter slightly less than the inside diameter of the trephine. The resulting circular gap provides a vacuum channel. In operation, prior to the parallel or lateral cut across the cornea made by a waterjet, the trephine makes a shallow, circular, perpendicular cut into the cornea with a cut diameter of 8 mm or more. This isolates a perfectly circular portion of the anterior cornea surface from the surrounding cornea. A narrow, circular trench forms as the lateral tension stretching the circular center is relaxed. The center section diameter decreases slightly and the outside section pulls away slightly since it is no longer pulled by the center section. This now independent circular section rises slightly, exposing its sides and nestled into the trephine/template space. The main body of the cornea is not changed and the anterior shape is maintained. When the vacuum template flattens the anterior surface and the waterjet begins its cut, the waterjet first encounters these perpendicular stromal sidewalls and begins and ends the cut at these sidewall boundaries. It is perfectly analogous to cutting across a piece of circular cylindrical salami near and parallel to its end with a large diameter circular, rotating blade .

The quality of cuts made in accordance with the method of the present invention is outstanding. They are so clean that one can observe the individual lamellar bands and undamaged fibrils running across the surface. This means that the cuts are truly lamellar in nature. Keratocytes are left in place and intact. There is a mathematical basis for calculating the required shape of a template to achieve the desired shape of the excision during the power cut. This is based on a spatial transform in conjunction with 2-dimensional Fourier transform analysis. From the required shape of the cornea surface during the cut, the transform allows calculation of the necessary shape of the template to achieve the desired corneal shape.

DETAILED DESCRIPTION OF THE DRAWINGS AND THE PREFERRED EMBODIMENT

Figure 2:
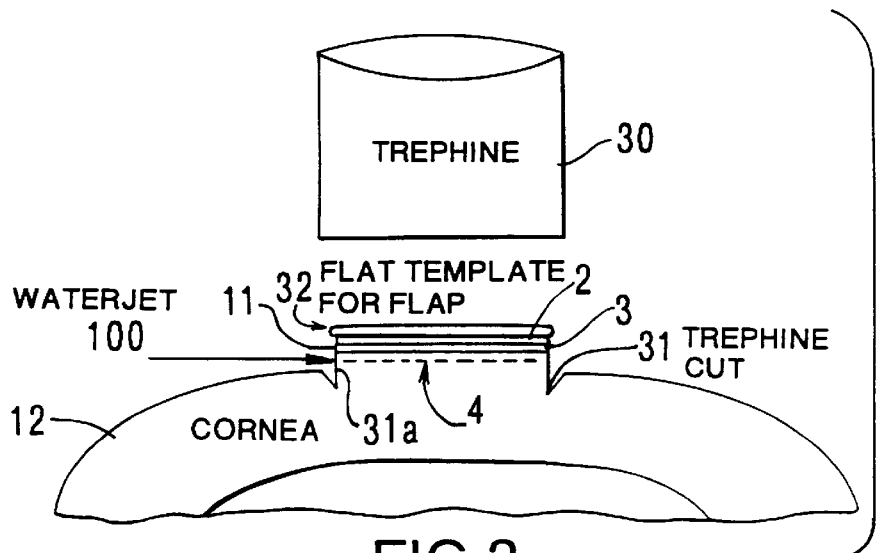
FIG. 2 depicts the scoring of the corneal tissue with a surgical trephine in combination with a flat template, in accordance with the present invention wherein sub-surface tissue is exposed for lateral cutting without cutting of the low sectility corneal surface layers.

With specific reference to the drawings, in FIG. 1, cornea 10 of eye 1 is shown with respective epithelium layer 2, Bowman's layer 3 and the underlying tissue, i.e., sub-surface stroma 4. As shown, a lateral cut by waterjet 20 (or a microkeratome, not shown) first encounters the epithelium layer then the Bowman's layer prior to effecting a lateral cut 21 in the stroma. As shown in FIG. 2, prior to lateral cutting, the corneal tissue is scored with a circular trephine 30 to provide score 31 which assumes the gutter shape depicted in the shape of a "v". This results from a release in stress of region 11 from the remainder of cornea 12. At the same time region 11 contracts and becomes elevated from the remainder of the cornea 12, with sub-surface stroma 4 becoming laterally accessible above gutter or score 31, whereby waterjet 100 can directly cut into the stroma without first encountering epithelium and Bowman's layers 2 and 3.

Figure 3:
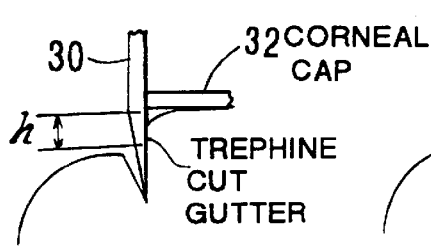
FIG. 3 depicts a combination of template and trephine therewithin, in accordance with the present invention.
Figure 3A:
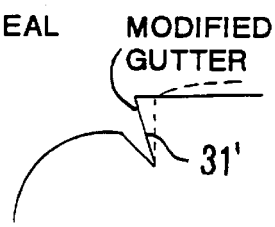
FIGS. 3a and 3b depict variations of alternative non-normal, angular score configurations.
Figure 3B:
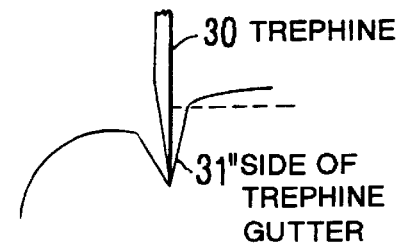

Flat circular template 32, originally closely fitted within trephine 30, fits substantially exactly on region 11 (which has been stress relieved to a slightly smaller diameter) to hold and shape the stroma for the planar cut shown. Though the preferred normal cut is shown in FIG. 2 (with vertical gutter walls 31a) which results in section slices of a cylinder, other angled cuts 31' and 31" shown in FIGS. 3a and 3b respectively of inwardly and outwardly angled scores. In such embodiments, the templates are matched according to the score for effective vacuum fitting.

It is understood that the above examples and drawings are merely illustrative of the present invention. Thus, for example while the present invention has been described for use with a waterjet cutting device, other cutting devices may be utilized though to lesser effect. These and other changes may be made in the procedure and the devices used in the procedure without departing from the scope of the present invention as defined in the following claims.

What is claimed is:

1. A method of effecting facilitated lateral cuts of normally stressed sub-surface tissue, comprising the steps of:
   a) peripherally shallowly scoring an area of the sub-surface normally stressed tissue, which is to be laterally cut, to a depth whereby the sub-surface tissue is released from lateral stress and becomes exposed for lateral cutting access at the score site; and
   b) effecting at least one lateral cut into the exposed sub-surface tissue.

2. The method of claim 1, wherein the sub-surface tissue is corneal stroma tissue and wherein the cornea is restrained from movement during said scoring and lateral cut.

3. The method of claim 2, wherein the lateral cut is effected by a waterjet.

4. The method of claim 3, wherein the scoring is effected by a circular trephine.

5. The method of claim 4, wherein the cornea is restrained from movement, during the effecting of the lateral cut, by means of a vacuum template contained within said trephine and said vacuum template is fitted on said area after the peripheral scoring.

6. The method of claim 2, wherein the area is completely scored and wherein a first lateral cut is terminated before completing passage across the sub-surface tissue wherein a residual portion remains of the sub-surface tissue sufficient to function as a hinge for a flap formed at an end of the lateral cut.

7. The method of claim 6, wherein the scoring is in a direction normal to the cornea.

* * * * *